United States Patent [19]

Deckner

[11] Patent Number: 5,405,392
[45] Date of Patent: Apr. 11, 1995

[54] ARTICULAR PROSTHETIC DEVICE

[76] Inventor: André G. Deckner, 5 rue del'Harmonie, 75015 Paris, France

[21] Appl. No.: 73,777

[22] Filed: Jun. 8, 1993

[30] Foreign Application Priority Data

Jun. 10, 1992 [FR] France .................. 92 06955

[51] Int. Cl.⁶ .......................... A61F 2/30; A61F 2/32
[52] U.S. Cl. .......................................... 623/18; 623/22
[58] Field of Search ........................ 623/16, 18, 19, 22, 623/23

[56] References Cited

U.S. PATENT DOCUMENTS

| | | | |
|---|---|---|---|
| 4,624,674 | 11/1986 | Pappas et al. | 623/22 |
| 4,681,589 | 7/1987 | Tronzo | 623/22 |
| 4,798,610 | 1/1989 | Averill et al. | 623/22 |
| 4,878,918 | 11/1989 | Tari et al. | 623/22 |
| 4,919,674 | 4/1990 | Schelhas | 623/22 |
| 5,062,853 | 11/1991 | Forte | 623/22 |
| 5,092,897 | 3/1992 | Forte | 623/22 |
| 5,263,988 | 11/1993 | Huebner | 623/22 |

FOREIGN PATENT DOCUMENTS

| | | | |
|---|---|---|---|
| 2638963 | 5/1990 | France | 623/22 |
| 2903366 | 8/1979 | Germany | 623/22 |

Primary Examiner—Randall L. Green
Assistant Examiner—Mary Beth O. Jones

[57] ABSTRACT

Articular prosthetic device which comprises: a half-shell having an inner surface and an insert having an outer surface, the inner surface of the half-shell and the outer surface of the insert being shaped so that the insert is retained within the half-shell when it is pushed therein, by applying a force thereto directed along an axis of impaction, with surface contact between the two mating surfaces, the outer surface of the insert comprising a plurality of sections, each section forming, in cross-section, with the impaction axis, an internal angle of less than 12°, the inner surface of the half-shell comprising portions mating with the sections and forming in cross-section, with the impaction axis, an external angle substantially equal to the internal angle.

10 Claims, 4 Drawing Sheets

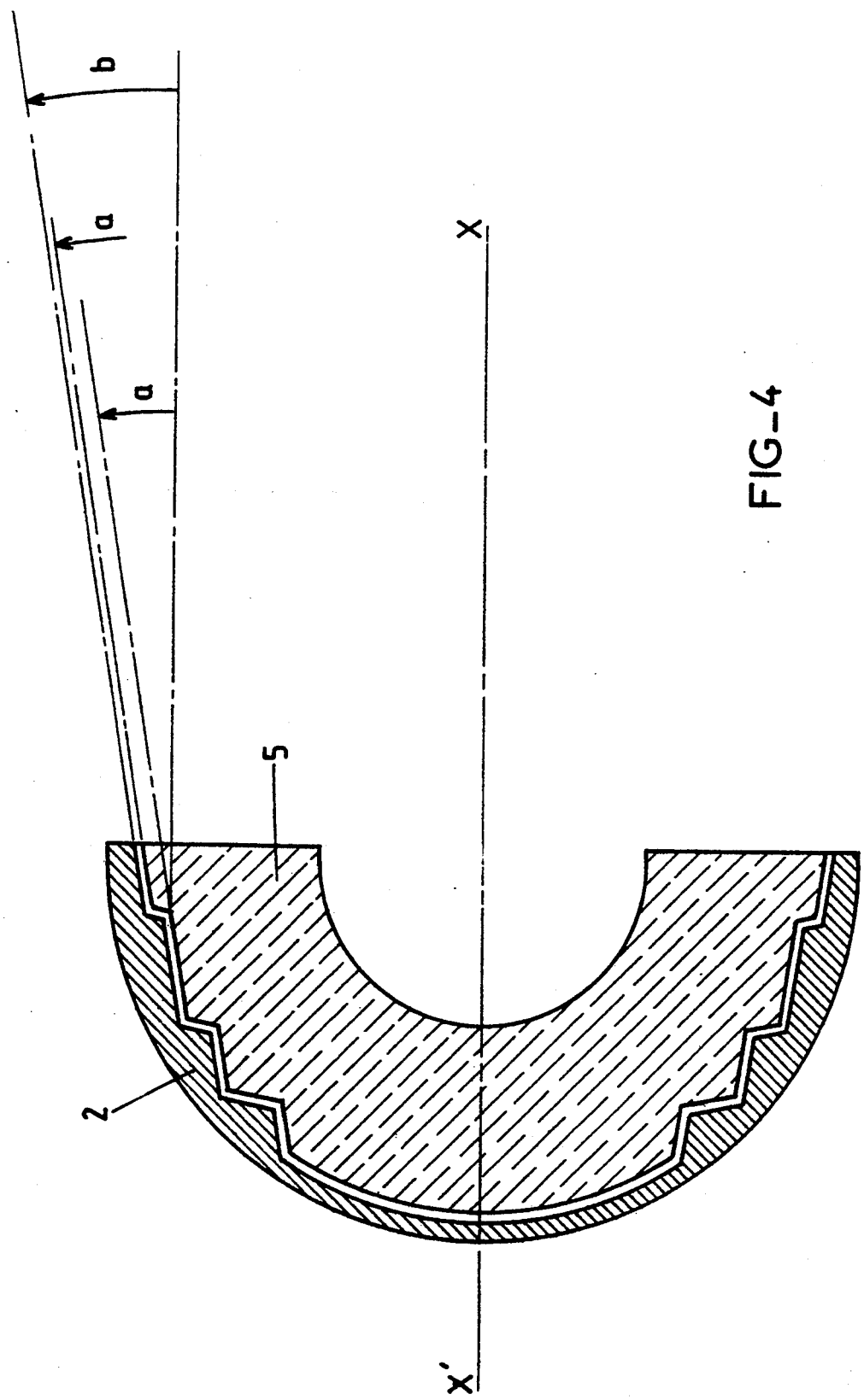

ARTICULAR PROSTHETIC DEVICE

The invention relates to articular prosthetic devices of a half-shell construction for human and animal joints, which may assume a conical surface type configuration, such as a spherical surface or enarthrosis, an ellipsoidal surface or condylarthrosis or, finally, a curvilinear surface referred to as a saddle or pedarthrosis.

The term "conical surface" is taken here in the broad sense of assuming the configuration of a cone, i.e. a surface generated by a moving straight line (generatix or generator line) which passes through a fixed point (vertex) whilst resting on a curve (directrix).

Generally, any articular prosthesis is intended to connect a defective member, which may be referred to as the supporting bone, functionally to another defective member which is the supported bone.

This type of prosthesis is frequently found in the human hip, which presents major mechanical problems which have to be resolved because of the fact that it has the largest amplitude of movement under the highest load, which may sometimes exceed 100 kg with substantial pounding caused by walking, for periods of 10 to 20 years or more, and which may be subjected to a million steps per year.

When surgery of this kind is carried out, a femoral head fixed to the femur is put in place on the side of the supporting bone and an implant is put in place on the side of the supported bone.

The operation may be carried out on one or other of these elements or on both.

Usually, connections of articular prostheses using a loose fit between the elements with inserts of conical or spherical or some other type did not give satisfaction owing to the fact that residual play was always present during use.

It should be noted that, even though an artificial hip joint is mechanically difficult to produce, the shaping of another joint such as the knee joint, of the pedarthrosis type, is among the most complex to resolve from the geometric point of view, in addition to the stresses referred to above.

The invention relates to an articular prosthetic device which, whilst providing a connection without play or friction between the half-shell and the insert, even if these two components are of different materials as is usual, makes it possible to adapt to a relatively thin and hence flexible half-shell, so as to follow the deformations of the pelvis when the patient walks, whilst at the same time allowing the outer surface of the half-shell to be made in any desired shape so as to be able to fit any cavity.

The device according to the invention comprises a half-shell and an insert, the inner surface of the half-shell and the outer surface of the insert being shaped so that the insert is retained within the half-shell after being placed therein, by applying a force directed along an impaction axis, with surface contact between the two mating surfaces, the outer surface of the insert comprising a plurality of sections, each section forming in cross-section with the impaction axis an internal angle of less than 12° and, preferably less than 8°, and cooperating with a mating portion of the internal surface of the half-shell, forming in cross-section with the impaction axis an external angle substantially equal to the internal angle, e.g. equal to the latter within ±2° and, particularly, within ±1°. Thanks to these sections having conical surfaces, at least two of which each have a generator at least 1 mm long, in relation to the impaction axis, a conical connection is provided between the half-shell and the insert, this connection being reliable even if the internal general shape of the half-shell forms an angle of more than 12° with the impaction axis, an angle which is known not to provide satisfactory fixing in the cooperation of two conical surfaces according to the so-called morse cone system. The absence of friction results in an absence of wear and removal of material, with the result that the prosthesis does not become worn in the course of time.

The invention will be more fully understood from the remainder of the text, referring to the accompanying drawings.

In the drawings,

FIG. 4 is a schematic view illustrating the invention.

Figure 1:
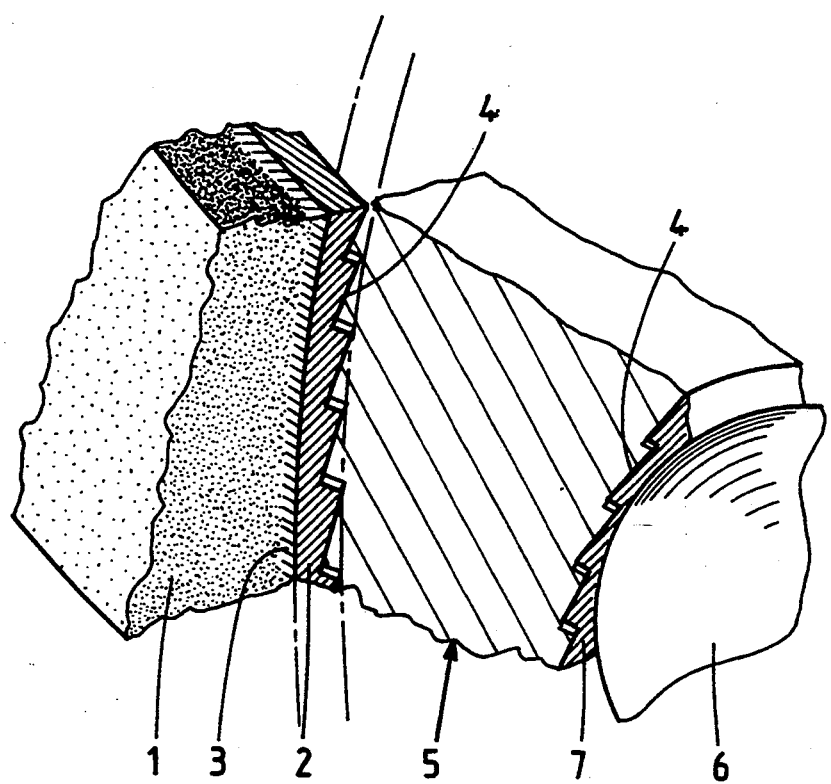
FIG. 1 is a highly schematic expanded view showing the assembly of the prosthetic device according to the invention.

FIG. 1, which is an expanded view of a theoretical prosthetic device, shows the supported bone 1 receiving the half-shell 2 by suitable fixing means 3; the half-shell 2 itself receives, by an interlocking fit 4, an insert generally designated 5 which is pushed in along the axis of impaction XX' (FIG. 2), i.e. the straight line along which the insert is pressed in, which is not necessarily an axis of symmetry, whilst the insert enables the swivelling head 6 to articulate, whether or not an interposed seat 7 is provided.

The machining of the bone 1 is conventionally known, as are the fixing means 3 which may consist of cementing, screwing by means of threaded screws or multiple screws, and also the head of the prosthesis, which may assume any desired dimensions according to the material of which it consists.

The fixing of the head of the prosthesis 6 to the supporting bone is conventionally known and not shown here.

In general and non-exclusive terms, the half-shell 2 may consist of titanium with a thickness compatible with a certain desired flexibility, preferably a wall thickness of less than 3 mm. The insert 5 is of solid construction of a material such as polyethylene and the seating is of a type compatible with the head, in order to provide optimum sliding and minimum wear.

Figure 3:
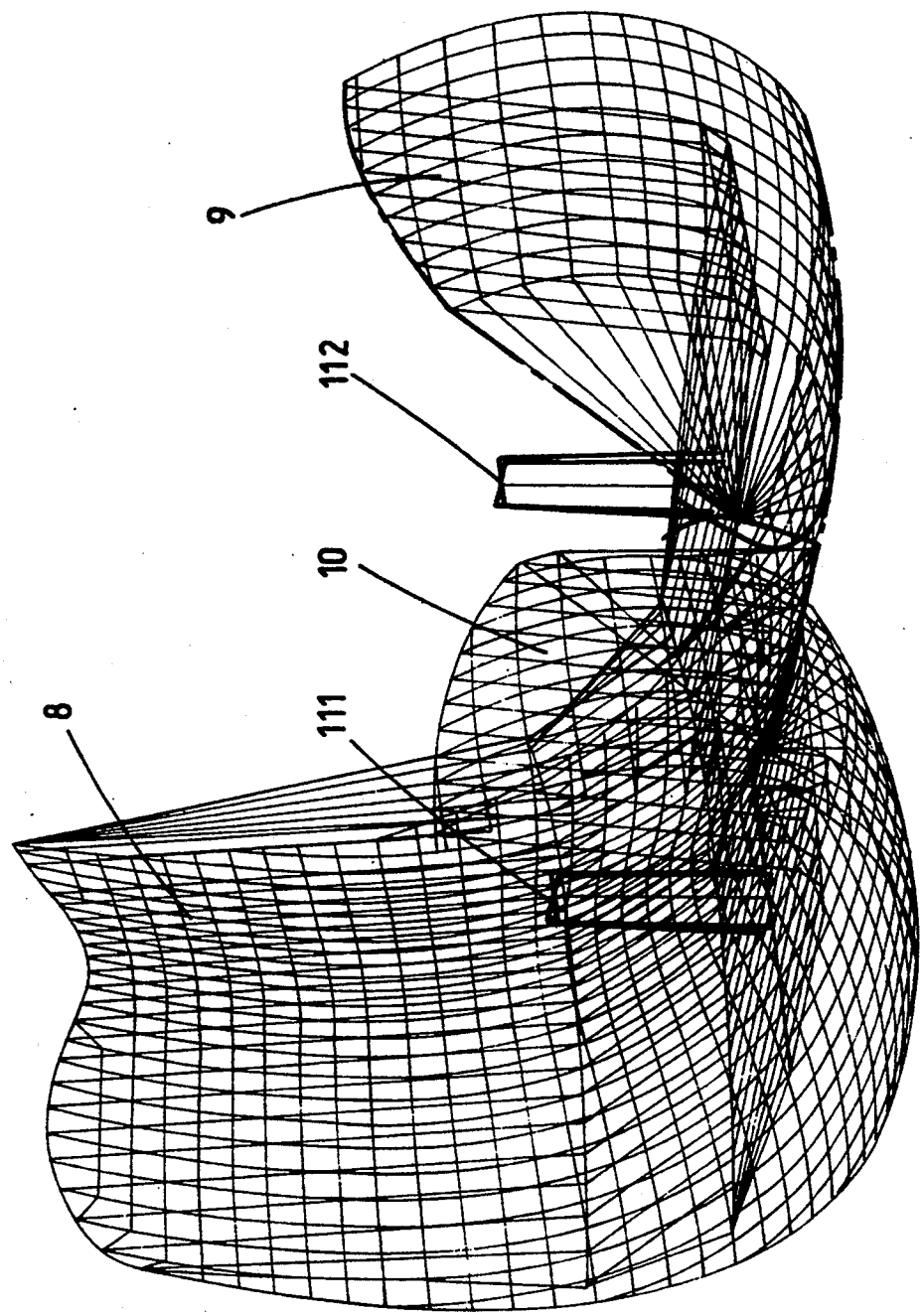
FIG. 3 is a perspective view of a knee joint indicated by dashes.

FIG. 3 shows the geometric complexity of a knee prosthesis or pedarthrosis-type joint on which it is shown that, as mentioned above, the surface 8 is an approximation of a conical surface element and the surfaces 9 and 10 are another approximation of two other conical surfaces; the invention may extend into the field of a joint of this kind without losing sight of the fact that the articulating surfaces of this kind are skew and highly complex.

The anchorage studs $11_1$ and $11_2$ act as means of attachment to the bone, for example.

Figure 2:
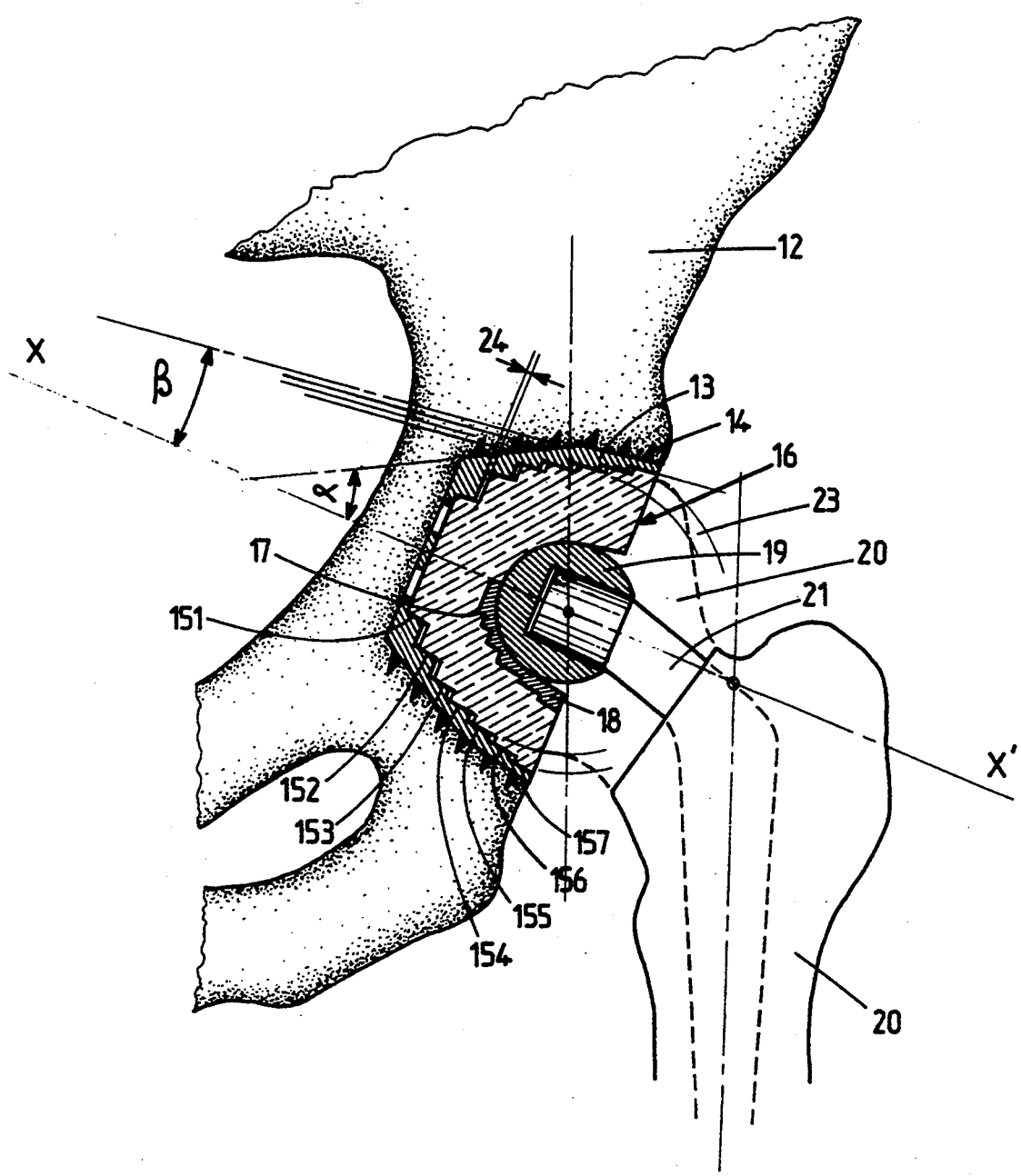
FIG. 2 is an elevational view in partial cross-sectional of a hip prothesis according to the invention.

FIG. 2 also shows the supported bone 12 receiving the half-shell 13 attached by fixing means which consist in this case of a screw thread 14. The outer surface of the half-shell 13 forms in cross-section with the impaction axis, and angle greater than 10 degrees. The half-shell 13 receives, by interlocking engagement with conical steps generally designated 15, an insert generally designated 16 which is capable of receiving, again by engagement with conical steps generally designated 17, a seating 18.

The insert articulates the femoral head 19 fixed to the supporting bone 20 by means of a conically interlocking support 21, the bone section 22 having been removed during the surgical operation.

In a diagram of this kind, the half-shell 13 "hugs" the cotyloid cavity in the space reserved for it 23 as closely as possible, with the result that, on the one hand, the angle is suitably determined and, on the other hand, the configuration of the steps $15_1$–$15_2$–$15_3$–$15_4$–$15_5$–$15_6$–$15_7$, which have unequal radial pitches, are also suitably determined. These steps may also have unequal axial pitches as well as different cone angles $\beta$; the latter is so that, for reasons of adapting to materials of very different kinds, the material the mass of which is most elastic can hug the shape of the least elastic material.

A space 24 is defined, as known in the art, to allow a force-fitted connection.

The interlocking engagement of the seat 18 in the insert 16 corresponds to analogous geometric, mechanical and physical conditions.

A type of interlocking connection of this kind with or without a seating, whether it be provided on a hip as shown in FIG. 2 or on any other joint as shown in FIG. 1, constitutes a self-locking assembly without play.

The diagram in FIG. 4 shows that the inner surface of the half-shell 2 has four steps, at least two of which form an angle of less than 8° with the impaction axis XX'. Similarly, the insert 5 comprises four sections which match the steps. The angle b of at least two of these sections with the impaction axis XX' is also less than 8°, the angles being viewed in the direction of the section in accordance with FIG. 4.

What is claimed is:

1. Articular prosthetic device which comprises: a half-shell having an inner surface and an insert having an outer surface, the inner surface of the half-shell and the outer surface of the insert being shaped so that the insert is retained within the half-shell when it is pushed therein, by applying a force thereto directed along an axis of impaction, with surface contact between the two mating surfaces, the outer surface of the insert comprising a plurality of sections, each section forming, in cross-section, with the impaction axis, an internal angle of less than 12°, the inner surface of the half-shell comprising a plurality of axially spaced steps mating with the sections, each of said steps comprising a pair of angularly intersecting surfaces, each step forming in cross-section, with the impaction axis, an external angle substantially equal to the internal angle of said associated mating section.

2. Device according to claim 1, wherein the internal angle is equal to the external angle to within ±2°.

3. Device according to claim 1, wherein the internal angle is less than 8°.

4. Device according to claim 1, wherein the half-shell has an outer surfaces forming in cross-section with the impaction axis, an angle greater than 10°.

5. Device according to claim 1, wherein at least two sections each have a generator line, relative to the impaction axis, of at least 1 mm.

6. Device according to claim 1, wherein the half shell has a wall thickness of less than 3 mm.

7. Device according to claim 1, wherein the sections are frusto-conical.

8. Device according to claim 1, wherein the steps have unequal radial pitches.

9. Device according to claim 1, wherein the steps have unequal axial pitches.

10. Device according to claim 9, wherein the steps have unequal radial pitches.

* * * * *